United States Patent [19]

Hittman et al.

[11] Patent Number: 5,650,759
[45] Date of Patent: Jul. 22, 1997

[54] FILTERED FEEDTHROUGH ASSEMBLY HAVING A MOUNTED CHIP CAPACITOR FOR MEDICAL IMPLANTABLE DEVICES AND METHOD OF MANUFACTURE THEREFOR

[75] Inventors: Fred Hittman; Allan S. Gelb; Marcia J. Gelb, all of Baltimore; Thomas N. Foreman, Ellicott City, all of Md.

[73] Assignee: Hittman Materials & Medical Components, Inc., Columbia, Md.

[21] Appl. No.: 555,396

[22] Filed: Nov. 9, 1995

[51] Int. Cl.⁶ ............................. H01G 4/35; H03H 7/01
[52] U.S. Cl. ..................... 333/182; 439/620; 607/37; 361/302; 333/185
[58] Field of Search ......................... 333/181–185; 439/620; 361/302; 607/37

[56] References Cited

U.S. PATENT DOCUMENTS

| | | | |
|---|---|---|---|
| 3,329,911 | 7/1967 | Schlicke et al. | 333/182 |
| 3,443,251 | 5/1969 | Garstang et al. | 333/182 |
| 3,617,830 | 11/1971 | Perna | 333/182 X |
| 3,879,691 | 4/1975 | Fritz | 333/182 |
| 4,152,540 | 5/1979 | Duncan et al. | 361/302 X |
| 4,314,213 | 2/1982 | Wakino | 333/182 |
| 4,424,551 | 1/1984 | Stevenson et al. | 361/302 |
| 4,642,589 | 2/1987 | Chambers | 333/182 |
| 4,673,900 | 6/1987 | Blamire et al. | 333/167 |
| 4,675,629 | 6/1987 | Sakamoto et al. | 333/182 |
| 4,682,129 | 7/1987 | Bakermans et al. | 333/184 |
| 4,698,605 | 10/1987 | Imamura et al. | 333/184 |
| 4,700,155 | 10/1987 | Sakamoto et al. | 333/182 |
| 4,700,440 | 10/1987 | Sakamoto et al. | 29/25.42 |
| 4,772,225 | 9/1988 | Ulery | 439/620 |
| 4,791,391 | 12/1988 | Linnell et al. | 333/184 |
| 4,804,332 | 2/1989 | Pirc | 439/620 |
| 4,819,130 | 4/1989 | Moy | 361/302 |
| 4,853,824 | 8/1989 | Tsuzurahara | 361/302 |
| 4,872,085 | 10/1989 | Tsuzurahara | 361/302 |
| 4,887,185 | 12/1989 | Okumura | 361/302 |
| 4,930,200 | 6/1990 | Brush, Jr. et al. | 333/185 X |
| 4,984,129 | 1/1991 | Tsuzurahara et al. | 361/302 |
| 5,030,875 | 7/1991 | Knecht | 310/346 |
| 5,032,949 | 7/1991 | Sasaki et al. | 361/302 |
| 5,150,086 | 9/1992 | Ito | 333/182 |
| 5,153,540 | 10/1992 | Gliha, Jr. | 333/182 |
| 5,206,786 | 4/1993 | Lee | 361/302 |
| 5,213,522 | 5/1993 | Kojima | 439/620 |
| 5,287,076 | 2/1994 | Johnescu et al. | 333/182 |
| 5,333,095 | 7/1994 | Stevenson et al. | 361/302 |
| 5,406,444 | 4/1995 | Selfried et al. | 361/302 |
| 5,493,259 | 2/1996 | Blalock et al. | 333/182 |

FOREIGN PATENT DOCUMENTS

| | | | |
|---|---|---|---|
| 6151014 | 5/1994 | Japan | 439/620 |

OTHER PUBLICATIONS

"Cellular Phones May Affect Use of Pacemakers", *The Wall Street Journal*, Friday, 28 Apr. 1995, pp. B1 and B3, Keller.
Makl, S., "EMI Filtering in Medical Implantables", *Medical Device & Diagnostic Industry*, Sep. 1994.
Barbaro, V., et al., "Do European GSM Mobile Cellular Phones Pose a Potential Risk to Pacemaker Patients?", *Pace*, vol. 18, Jun. 1995, pp. 1218–1224.
Sarda, L., et al., "Ceramic EMI Filters—A Review", *Ceramic Bulletin*, vol. 67, No. 4, 1988, pp. 737–746.

*Primary Examiner*—Benny Lee
*Assistant Examiner*—Justin P. Bettendorf
*Attorney, Agent, or Firm*—Morton J. Rosenberg; David I. Klein

[57] ABSTRACT

A filtered feedthrough assembly (100, 100', 100'', 200, 200'', 300) for use in implantable medical devices is provided. The filtered feedthrough assembly provides at least one chip capacitor (110, 210) or an LC circuit coupled between a lead wire (12) and an end surface (18) of a metallic ferrule (14). The chip capacitor is secured in position by means of a [non-conductive film (122) and] conductive material (120) applied to opposing ends of the chip capacitor. The end portion of the feedthrough and chip capacitor may be encapsulated by an encapsulant (102) to provide a moisture resistant coating therefor.

40 Claims, 6 Drawing Sheets

FILTERED FEEDTHROUGH ASSEMBLY HAVING A MOUNTED CHIP CAPACITOR FOR MEDICAL IMPLANTABLE DEVICES AND METHOD OF MANUFACTURE THEREFOR

BACKGROUND OF THE INVENTION

1. Field of the Invention

This invention is directed to a filtered feedthrough assembly having at least one lead wire. In particular, this invention directs itself to a feedthrough assembly utilizing at least one chip capacitor coupled between a lead wire and a metallic ferrule. Still further, this invention directs itself to a filtered feedthrough for use in implantable medical devices wherein the capacitor is affixed in position by both conductive and non-conductive materials. Still further, this invention directs itself to a filtered feedthrough wherein any one of a plurality of capacitor elements can be individually replaced if found defective during testing.

2. Prior Art

Filtered feedthrough devices are well known in the art. The best prior art known to the Applicant include U.S. Pat. Nos. 3,329,911; 3,443,251; 3,617,830; 3,879,691; 4,152,540; 4,314,213; 4,424,551; 4,642,589; 4,673,900; 4,675,629; 4,682,129; 4,698,605; 4,700,155; 4,700,440; 4,772,225; 4,791,391; 4,804,332; 4,819,130; 4,853,824; 4,872,085; 4,887,185; 4,984,129; 5,032,949; 5,150,086; 5,153,540; 5,206,786; 5,213,522; 5,287,076; 5,333,095; 5,406,444; and the following publications: "Cellular Phones May Affect Use of Pacemakers", *The Wall Street Journal*, Friday, Apr. 28, 1995, pp. B1 and B3; "EMI Filtering in Medical Implantables", *Medical Device and Diagnostic Industry*, September 1994; "Do European GSM Mobile Cellular Phones Pose a Potential Risk to Pacemaker Patients?", *Pace*, Vol. 18, June 1995, pp. 1218–1224; and, "Ceramic EMI Filters—A Review", *Ceramic Bulletin*, Vol. 67, No. 4, 1988, pp. 737–746.

Filtered feedthrough devices have been employed in implantable devices, as disclosed in U.S. Pat. No. 4,152,540 and the publication entitled "EMI Filtering in Medical Implantables". Such filtered feedthrough devices are known to employ discoidal capacitors in single lead feedthrough devices and discoidal capacitor arrays in multi-lead assemblies. However, while discoidal capacitor arrays can be very space efficient, a single faulty capacitive element in such discoidal arrays caused the loss of an entire device, as such capacitive elements were not individually repairable and were very difficult to remove once installed. Further, the feedthrough devices incorporating such capacitive elements had to be specially manufactured to provide a cavity into which the capacitor or capacitor array was to be located, either by creating a recess within the ceramic hermetic sealing element, or extending the metallic ferrule beyond the hermetic seal in order to form such a cavity. Thus, even where a single discoidal capacitor is employed, such becomes extremely difficult to replace after having been bonded in position within such a cavity. Whereas in the instant invention, individual chip capacitors are utilized and positioned either on an end surface of the hermetic seal insulator or on a separate substrate which is subsequently married to the feedthrough. By this arrangement, filtering can be added to a conventional feedthrough device without the requirement for manufacturing special parts, thereby improving the efficiency of the manufacturing operation and allowing replacement of any chip capacitor with relative ease.

In still other prior art devices, such as that disclosed in U.S. Pat. No. 3,617,830, filtered feedthrough devices utilizing chip capacitors are disclosed. Such prior art devices disclose chip-type filter capacitors positioned between a pair of conductive rings, with the space between capacitors and the rings being encapsulated with an epoxy filler material. In addition to such materials not providing a high reliability hermetic seal, nor providing a biocompatible structure, such structures do not provide for accommodating capacitors of different sizes, as each chip capacitor is located within a cavity defined by the space between the conductive rings. Therefore, a different diameter outer ring is required for an application requiring larger capacitors, and in any one application all of the capacitors must be of the same length irrespective of their capacitive value. With the chip capacitors being disposed within a cavity, the difficulty in replacing any one capacitor which proves to be defective is almost as difficult as in the case where discoidal capacitors are utilized.

In systems such as that disclosed in U.S. Pat. No. 4,152,540, and other prior art systems such as that disclosed in U.S. Pat. Nos. 4,424,551 and 5,333,095, filtered feedthrough devices employing discoidal type capacitors are electrically coupled to the respective lead wires and ferrules utilizing conductive adhesive compositions. However, such systems provide no means by which defective devices can be easily replaced. Further, the system disclosed by U.S. Pat. No. 5,333,095 provides no means for applying a moisture resistant coating to the discoidal capacitive element which has a diameter substantially larger than that of the feedthrough device, making such impractical for use in most modern implantable systems wherein space is at a premium and where the feedthrough devices are manufactured by other than the implantable device manufacturer.

Outside the feedthrough art, it is known that chip capacitors may be employed in combination with ferrite blocks in connectors to form electromagnetic interference filters and electrically connected between the connector pin and the connector housing, as disclosed in U.S. Pat. No. 5,213,522. While a capacitive-inductive filter is formed by this arrangement, the individual capacitive elements are not easily replaced subsequent to their installation, as each capacitor is disposed within a cavity formed in a ferrite block, with the ferrite block being disposed within a cavity formed by the connector housing.

It has long been known that medical implantable devices must operate in an environment which is subjected to electromagnetic interference (EMI). The electrical leads which extend from such implantable devices act as antennas which receive and conduct electromagnetic energy into the electronics of the implanted device. Since the circuits of such medical implantable devices are very sensitive, and reliability is so important, as a fault may be life threatening, the medical implantable devices have incorporated filter circuits therein to suppress EMI. In some cases, feedthrough devices employing discoidal type capacitors have been employed in an attempt to filter out the electromagnetic interfering signals before they reach the electronic circuitry of the implantable device. The ability to filter the interference before it reaches the electronics has become more important recently, with the discovery that the electromagnetic interference generated by the new digital cellular telephones and other electronic devices is not sufficiently suppressed by prior art electromagnetic interference filters of some current medical implantable devices. The high frequency emissions from digital cellular telephones may be re-radiating within the medical implantable device, bypassing and thereby rendering the "on-board" filters ineffective. It is therefore critical that the filtering take place as close to the source of the emissions as possible, such as at the entrance to the housing of the implantable device. As a result of this ever increasing problem, the use of filtered feedthroughs will be required to effectively suppress EMI, and therefore it will be important to efficiently manufacture such in order to help contain the costs of the implantable medical devices. Thus, it will be important to be able to avoid the scrapping of whole assemblies when one component thereof is found to be defective.

Further, for medical devices such as implantable defibrillators, the high voltage output through the feedthrough devices adds another complexity to incorporating a filter capacitor therewith. A capacitor employed in such a device must be physically larger in order to withstand the higher voltage which will be impressed thereon, but the space limitations of the feedthrough used in such defibrillators are not conducive to accommodating large-sized capacitors. However, utilizing the filtered feedthrough of the present invention, such larger capacitors can be installed without requiring an increase in the physical size of the feedthrough structure. Additionally, by the arrangement of the filtered feedthrough of the present invention, any capacitive element found to be defective can be replaced, thereby avoiding the necessity for scrapping a complete assembly, or even a capacitive subassembly. Still further, to suppress high frequency EMI, each lead of a multi-lead feedthrough may be required to be individually tuned. Thus, each lead may require a capacitor having a different capacitance, voltage rating, or the like, which can be installed in the present invention.

SUMMARY OF THE INVENTION

A filtered feedthrough assembly for medical implantable devices is provided. The filtered feedthrough assembly includes a metallic ferrule having opposing first and second ends and a centrally disposed through opening extending between the first and second ends. The ferrule has a flange formed on the first end thereof for coupling to a medical implantable device. The filtered feedthrough assembly further includes at least one elongate lead wire having a circular cross-sectional contour extending through the ferrule through opening. The filtered feedthrough assembly is also provided with an assembly for forming a hermetic seal between the lead wire and the ferrule disposed within the ferrule through opening. At least one chip capacitor having a parallelepiped contour is also provided on the end surface of the hermetic seal assembly, and extends from the lead wire to the ferrule. The chip capacitor has a pair of metallized contacts formed on opposing end portions thereof. Material is provided for electrically coupling the metallized contacts of the chip capacitor to the lead wire and the ferrule, respectively.

DESCRIPTION OF THE PREFERRED EMBODIMENTS

Referring to FIGS. 3–22, there is shown, filtered feedthrough assemblies 100, 100', 100", 200, 200', 200" and 300 for use in implantable medical devices. Implantable devices utilized in the medical and biological sciences that require signals to be input thereto, or provide output signals are susceptible to interference from various sources of electromagnetic radiation. In addition to such implantable devices requiring protection from spurious electromagnetic radiation, these devices must be protected from infiltration of bodily fluids and migration of toxic materials therefrom.

Figure 1:
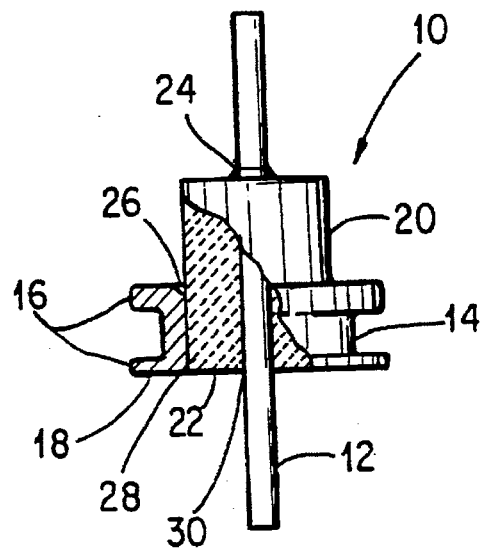
FIG. 1 is an elevation view, partially cut-away, of a conventional feedthrough device.

The most common implantable medical devices in use today are pacemakers, and defibrillators. Both of these devices require one or more electrodes to be coupled from the device to the implant recipient's heart muscle. The electronics for such devices are typically housed in a titanium case which is hermetically sealed, as by laser welding. The electrical connection between the electronics within the housing and the external electrodes is made through a device known as a feedthrough, such as feedthrough 10, shown in FIG. 1.

The conventional feedthrough 10, is shown as being a single lead feedthrough, however, such devices are readily available in multiple lead assemblies, which may have any number of leads, and are commonly produced with two, three, four, five or six leads. Feedthrough 10 includes a metallic ferrule 14 having a central through opening 28 formed therein. Ferrule 14 may have one or more flanges 16 formed therein to facilitate mounting to the implantable medical device, and may be circular, oblong or rectangular in cross-sectional contour. Ferrule 14 may be formed of materials such as titanium, niobium, tantalum, or alloys thereof. A lead wire 12 extends through the opening 28 and is sealed with an insulator 20, the insulator 20 having a central through bore 30 for passage of the lead wire 12 and an outside diameter dimensioned to fill the remainder of opening 28. Lead wire 12 may be formed of materials such as platinum, platinum/iridium, niobium, titanium, tantalum, or combinations thereof. The insulator 20 may be a glass composition wherein metal-to-glass seals are formed at the perimeter of the openings 28 and 30. Insulator 20 may alternately be formed of a ceramic material composition, in which case the insulator is bonded to the lead wire 12 and ferrule 14 by the brazed joints 24 and 26, respectively. The brazed joints 24 and 26 may be accomplished with such materials as gold, a gold alloy or a titanium alloy.

Feedthrough 10 is provided with the insulator 20 having an end surface 22 that is disposed in coplanar relationship with the end surface 18 of ferrule 14, the end surfaces 18 and 22 being disposed within the housing of the implantable medical device, allowing conduction of signals on the lead wire 12 while maintaining a hermetic seal. Alternately, the sides of the ferrule can be extended to form a well into which filter capacitors will be disposed.

Figure 2:
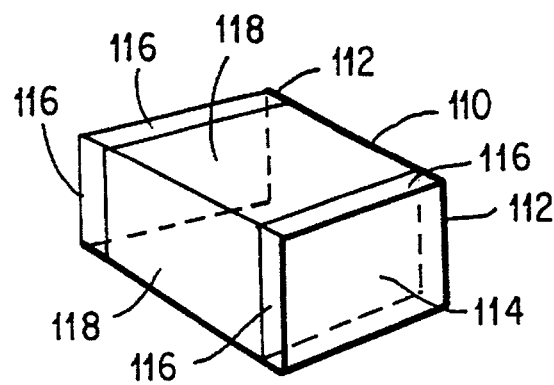
FIG. 2 is a perspective view of a chip capacitor utilized in the present invention.

Referring now to FIG. 2, there is shown, a "chip capacitor" 110, a commercially available device having a parallelepiped ceramic body with a pair of metallized contacts 112 formed on opposing ends thereof. Each metallized contact 112 includes a conductive end portion 114 and a plurality of conductive segments 116 disposed on each side 118 of chip capacitor 110, at the endmost regions thereof. By such arrangement, electrical coupling can be made with side portions of the chip capacitor, as well as end portions thereof.

Figure 3:
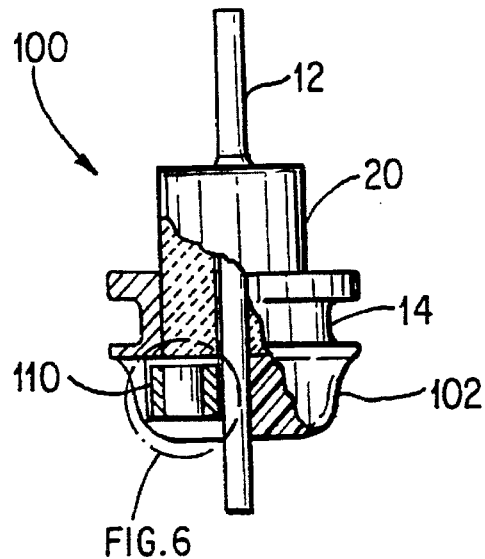
FIG. 3 is an elevation view, partially cut-away, of a single lead embodiment of the present invention.

A filtered feedthrough 100 is constructed utilizing a chip capacitor 110 which is added to the feedthrough 10, as shown in FIG. 3. Although only one capacitor 110 is shown, it should be understood that multiple capacitors may be coupled to lead wire 12. Chip capacitor 110 is electrically coupled to lead wire 12 on one end, and electrically coupled to the ferrule 14 on the opposing end. Subsequent to the installation of capacitor 110, such may be encapsulated utilizing an encapsulant 102 in applications requiring such. The encapsulant 102 may be any of a large number of moisture resistant polymers. In one working embodiment, a potting compound having the trade name "ABLEBOND 933-1" was successfully utilized as encapsulant 102.

Figure 6:
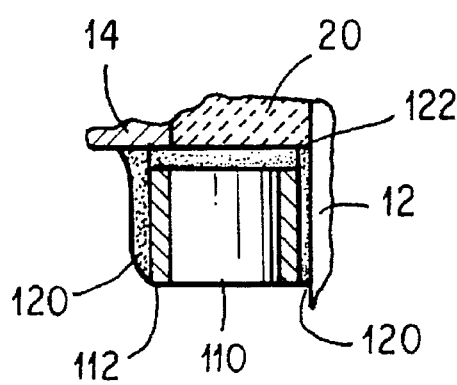
FIG. 6 is an enlarged portion of the elevation view of FIG. 3 showing the mounting of a chip capacitor.

As shown in FIG. 6, the capacitor 110 is installed on the interior facing side of the feedthrough 10 and may be secured by means of a non-conductive film 122 applied to a side surface of capacitor 110, with that side surface then being juxtaposed on the end surface 22 of the insulator 20, the capacitor being radially oriented to extend from the lead wire 12 across the insulator 20 to the ferrule 14. Non-conductive film 122 may be formed from a glass composition, a flux paste, a polyimide, epoxy, or other polymer composition. In one working embodiment, a non-conductive polyimide adhesive having the trade name "ABLEBOND 71-2" was successfully utilized as the non-conductive film 122. Subsequent to positioning of capacitor 110, conductive material 120 may then be added at each of the metallized contacts 112 to make respective electrical connections to the lead wire 12 and ferrule 14. The electrically conductive material 120 may be a solder or braze material, or alternately a conductive glass, conductive epoxy, or conductive polyimide composition. A commercially available conductive polyimide composition having the trade name "ABLEBOND 71-1" has been successfully utilized for providing electrical coupling of capacitor 110.

Where the non-conductive film 122 and conductive material 120 are adhesive compositions, after installation of the chip capacitors the filtered feedthrough assembly is heated to cure such compositions prior to the step of encapsulating the installed capacitor. Subsequent to application of the encapsulant 102, such may be cured by heating the completed unit for a predetermined time period. Where the conductive material 120 is a solder or braze material, the capacitor 110 is not affixed to the feedthrough 10 utilizing the non-conductive film. However, if temporary securement is desired, a flux paste may serve that purpose.

Figure 4:
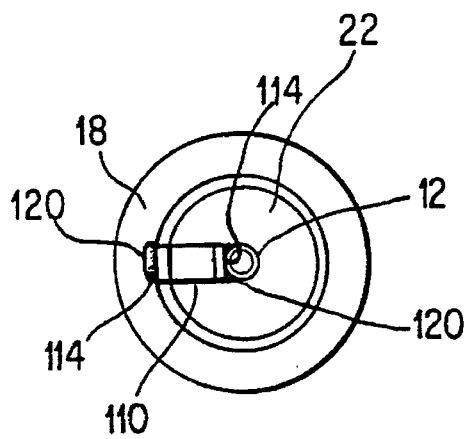
FIG. 4 is a bottom plan view of the embodiment of FIG. 3.

As shown in FIG. 4, capacitor 110 has a first end 114 disposed in contiguous relationship with the lead wire 112, the capacitor extending radially therefrom to the ferrule 14, wherein the opposing second capacitor end surface 114 is electrically coupled to the end surface 18 of ferrule 14 utilizing the conductive material 120. Conductive material 120 likewise applied to the first end surface 114 and lead wire 12 to provide electrical coupling therebetween.

Figure 5:
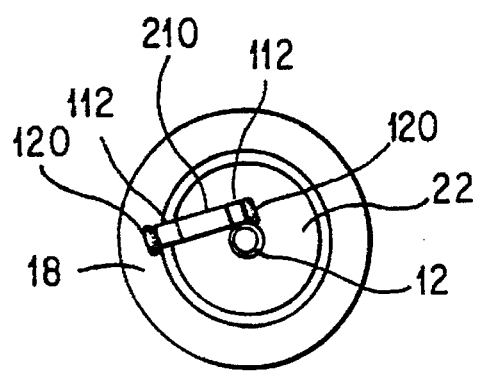
FIG. 5 is a bottom plan view of an alternate configuration of the embodiment of FIG. 3.

Referring now to FIG. 5, there is shown, an alternate configuration for mounting a chip capacitor 210 to the feedthrough 10. Chip capacitor 210 is a physically larger device than capacitor 110. Where capacitor 210 is of sufficient length such that it cannot be mounted in the same manner as capacitor 110, as it would leave inadequate space for the encapsulant 102, or extend beyond the ferrule, or create a mechanical interference with some portion of the implantable medical device to which filtered feedthrough 100 is to be applied. The capacitor 210 is mounted with one of the side conductive segments 116 disposed in contiguous relationship with the lead wire 12, and extends radially therefrom to the ferrule 14. As in the embodiment of FIG. 4, conductive material 120 is applied to the opposing ends of the capacitor 210, to provide an electrically conductive bridge between the metallized contacts 112 and the lead wire 12 and end surface 18 of ferrule 14, respectively. By means of offsetting capacitor 210, a physically larger capacitor is accommodated. This is of particular importance, as the feedthroughs utilized in implantable medical devices are of very small size, ranging in diameter from 0.142 inch for a single lead assembly to 0.246 inch for a six lead assembly, at their greatest dimension. In defibrillator applications, the voltages impressed across the filter capacitor 210 are relatively large, thereby requiring a capacitor of substantial size. By the arrangement shown in FIG. 5, it is possible to provide a filtered feedthrough for such applications without increasing the diameter of the feedthrough.

Figure 13:
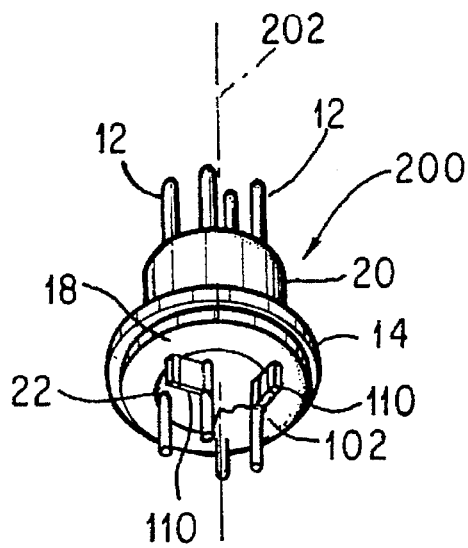
FIG. 13 is a perspective view of a multi-lead embodiment of the present invention.

Referring now to FIG. 13, there is shown, a four conductor filtered feedthrough 200. The four lead filtered feedthrough 200 is shown as an example of a multi-lead feedthrough device, but in actuality it may have any number of leads radially spaced about the feedthrough central axis 202.

Figure 14:
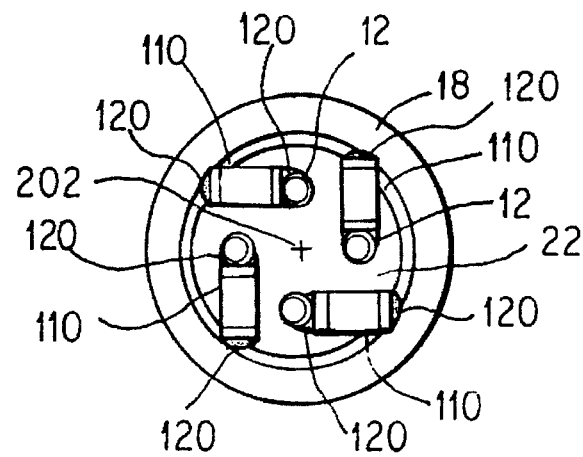
FIG. 14 is a bottom plan view of the multi-lead embodiment shown in FIG. 13.
Figure 17:
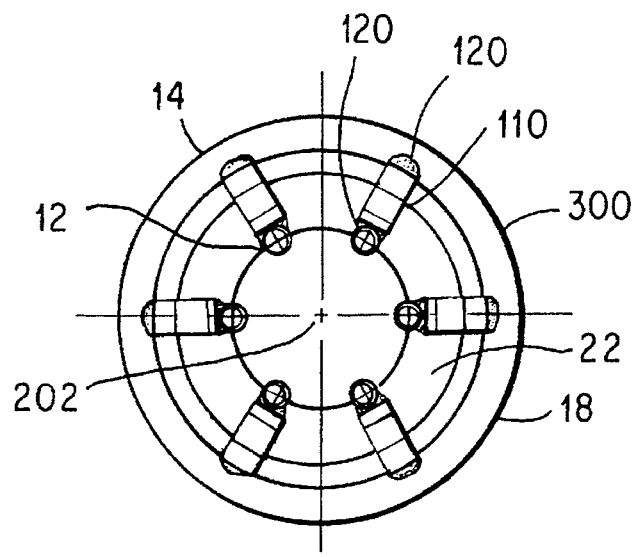
FIG. 17 is a bottom plan view of another embodiment of the multi-lead version of the present invention.

Filtered multi-lead feedthrough 200 includes a plurality of lead wires 12 which extend through respective openings formed in the insulator 20, the combination being disclosed within a central opening formed in the ferrule 14, and with a hermetic seal being formed between each lead wire and the insulator 20 and between the insulator 20 and ferrule 14. Like in the single lead example, the end surface 22 of insulator 20 is shown to be coplanar with the end 18 of ferrule 14, however, it need not be. The arrangement in which the ferrule end surface 18 and insulator end surface 22 are coplanar is more prone to problems such as the conductive material 120 wicking under the capacitor and creating a short circuit, which problem is solved by the structures and methods described herein. As best shown in FIG. 14, each of the leads 12 is coupled to a respective filtering chip capacitor 110. As in the single lead version, each chip capacitor 110 extends from a respective lead wire 12 across the end surface 22 of insulator 20 to the ferrule end surface 18, electrical connection being made on opposing ends thereof by means of addition of the conductive material 120, the conductive material 120 providing conductive contact between the capacitor metallized contacts 112 and the respective lead wire 12 and ferrule end surface 18. As previously described, and shown in FIG. 6, the underside of each capacitor 110 may be provided with a non-conductive film which serves to bond the capacitor to the feedthrough assembly and prevent inadvertent flow of the conductive material 120 across the bottom of the capacitor. As shown in FIG. 17, the same arrangement is applicable to a six conductor feedthrough 300, with each capacitor 110 extending radially from a respective lead 12 across the end surface 22 of the insulator to the end surface 18 of the ferrule, with electrical contact being made by application of conductive material 120 to opposing ends of the capacitor.

Figure 15:
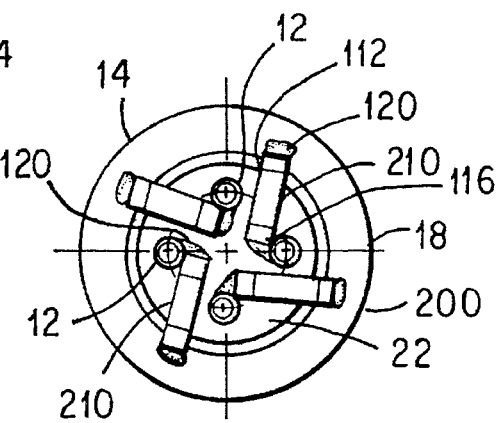
FIG. 15 is a bottom plan view of an alternate configuration of the embodiment shown in FIG. 13.

Turning now to FIG. 15, there is shown, an alternate means of mounting chip capacitors to accommodate capacitors having a larger physical size. As in the embodiment shown in FIG. 5, for the single conductor filtered feedthrough 100, four conductor filtered feedthrough 200 can accommodate the larger chip capacitors 210 in a similar manner. Each of the capacitors 210 is offset from a respective lead wire 12 such that the side conductive segment 116 for the respective capacitor is disposed in contiguous relationship with the lead 12, the capacitor extending radially therefrom across the end surface 22 of the insulator 20 and the end surface 18 of the ferrule 14. Although FIGS. 14 and 15 show all of the lead wires 12 being coupled to capacitors of one size or another, it is important to note that such just illustrates the possible capacitor orientations. Using the techniques illustrated, any one or more lead wires 12 can be coupled to a larger size capacitor, while other lead wires may be coupled to capacitors of other sizes. There is no limitation in the instant invention which requires all capacitors to be of the same physical size or capacitance value.

Figure 16:
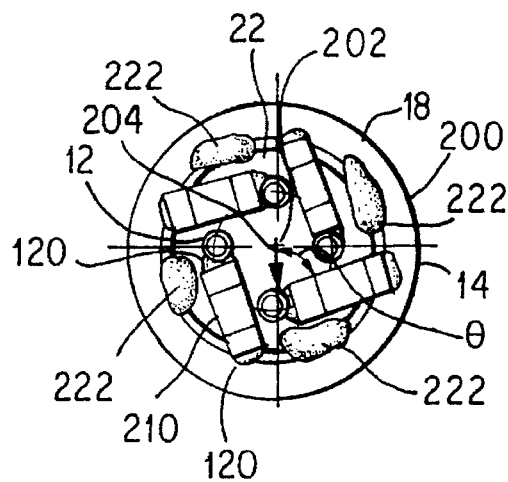
FIG. 16 is a bottom plan view of yet another alternate configuration of the embodiment of FIG. 13.
Figure 18:
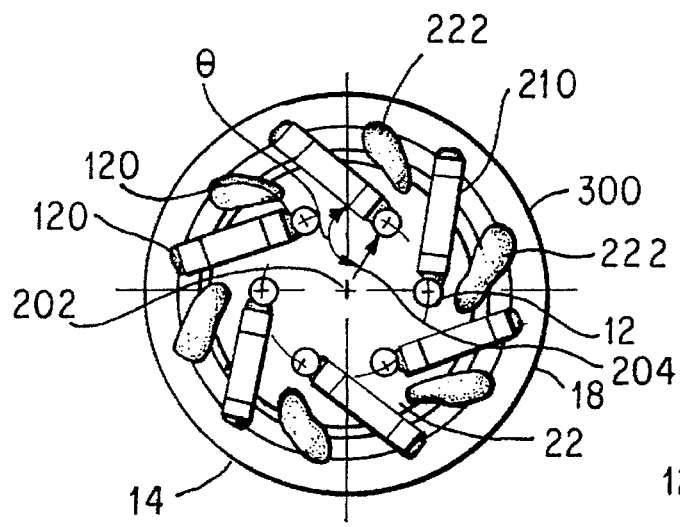
FIG. 18 is an alternate configuration of the multi-lead embodiment of FIG. 17.

Another method of installing larger type chip capacitors in a multi-lead feedthrough is shown in FIGS. 16 and 18. A four lead filtered feedthrough 200 is shown in FIG. 16 and a six lead filtered feedthrough 300 is shown in FIG. 18. In both embodiments, the plurality of lead wires 12 are equidistantly spaced radially from a central axis 202 of the respective feedthrough, and the respective chip capacitors 210 extend radially from a respective lead wire 12 at an angle $\theta$ with respect to a radial line 204 extending from the central axis 202 to the lead wire 12. The angle $\theta$ being within a range greater than 0°, but less than 90°. That orientation can be understood by comparing the embodiment of FIG. 16 with the embodiment of FIG. 14, wherein each of the capacitors is oriented at 90° with respect to a radial extending from the central axis 202 to the particular lead. The embodiment of FIG. 18, should be compared with the embodiment of FIG. 17, wherein each of the chip capacitors is oriented at an angle of 0° (180°) with respect to a radial extending from the central axis 202 to the particular lead wire. By virtue of orienting the capacitors at an angle $\theta$, larger chip capacitors 210 can be accommodated within the perimeter of the feedthrough device, which is less than 0.20 inch in diameter for the four lead version.

In addition to the application of a non-conductive film to the underside of each capacitor, as it is assembled, bands 222 of non-conductive film may be applied to a region adjacent each lead wire 12, and extending across the end surface 22 of insulator 20 to a portion of the end surface 18 of ferrule 14. The location of the non-conductive film bands 222 is intended to correspond to and be adjacent to the metallized contact portion of the respective chip capacitor which is disposed adjacent the respective lead wire 12. The band of non-conductive film prevents that metallized contact 112 or the conductive material 120 applied thereto from contacting the ferrule and thereby creating a short circuit.

Thus, in manufacturing such a multi-lead filtered feedthrough 200, 300, an insulating material composition such as a glass, polyimide, epoxy or other polymer is applied to an existing multi-pin feedthrough to form each of the plurality of bands 222. The subassembly is then heated to cure the insulating film. In one working embodiment, a commercially available polyimide composition having the trade name "ABLEBOND 71-2" has been successfully utilized to form the non-conductive bands 222, and is at least partially cured by heating the subassembly to 150° C. for approximately thirty minutes. Subsequently, the capacitors are installed. As shown in FIG. 6, a small quantity of a non-conductive film 122 is applied to a side surface of the chip capacitor, and that surface then juxtaposed over the end surfaces 22, 18 of insulator 20 and ferrule 14, with the capacitor being oriented radially from the lead wire 12, as has been described. Once the capacitor 210 (110) is positioned, the conductive material 120 is applied to opposing ends of the capacitor, to provide electrical contact, as well as mechanical structural support, between the opposing ends of the capacitor and the respective lead wire 12 and ferrule end surface 18. As previously discussed, the conductive material may be in the form of a conductive glass, conductive polymer, or a metallic composition to provide a soldered or brazed connection. Where a conductive polymer is utilized, the subassembled unit, a unit having the capacitors installed and non-conductive film 122 and conductive material 120 applied, is heated at a predetermined temperature to provide a partial cure thereof.

In one working embodiment, the non-conductive film 122 is formed by a polyimide composition having the trade name "ABLEBOND 71-2" and the conductive material composition is a conductive polyimide composition having the trade name "ABLEBOND 71-1". The polyimide compositions are then subjected to a first cure step, wherein the device is maintained at 150° C. for approximately thirty minutes. After cooling, the device is then electrically tested to insure that each capacitor meets the required specifications for the particular application. At this point in the process, if a capacitor is found to be defective, it can be easily repaired, as the polyimide compositions have not completed their curing process, allowing the defective capacitor to be removed and replaced by another part. Subsequent to insuring that each capacitor functions properly, the polyimide compositions are then fully cured by exposing the subassembly to a temperature of 275° C. for approximately thirty minutes. After fully curing the polyimide compositions and subsequent to cooling, the end of the device carrying the capacitors 210 is potted, encapsulating the capacitors in a moisture resistant composition, which may be an epoxy, polyimide, silicone or other polymer composition. The device is then heated at a predetermined temperature for a specified time period in order to cure the encapsulant. In one working embodiment, a polyimide composition having the trade name "ABLEBOND 933-1" was successfully utilized, and cured at a temperature of 125° C. for a time period approximating two hours.

Figure 7:
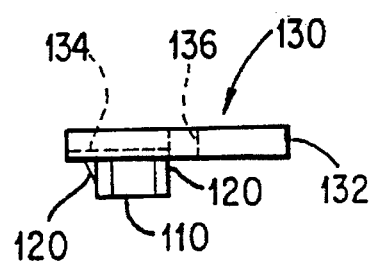
FIG. 7 is an elevation view of a capacitor support assembly of the present invention.
Figure 8:
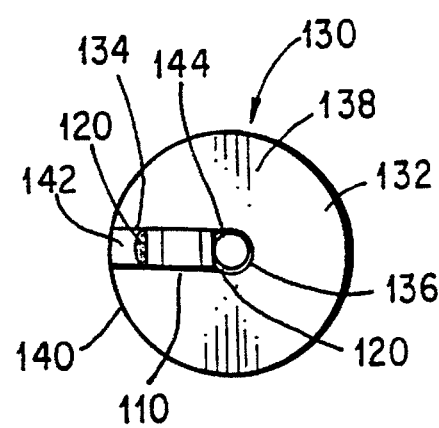
FIG. 8 is a bottom plan view of the capacitor support assembly of FIG. 7.
Figure 10:
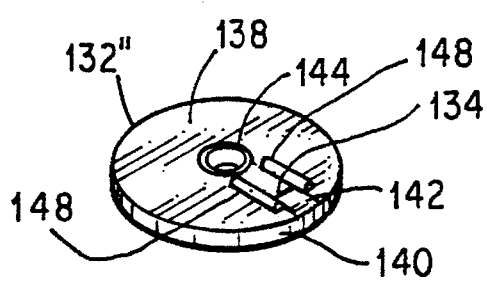
FIG. 10 is an alternate embodiment of the substrate of the capacitor support assembly of FIG. 7.
Figure 11:
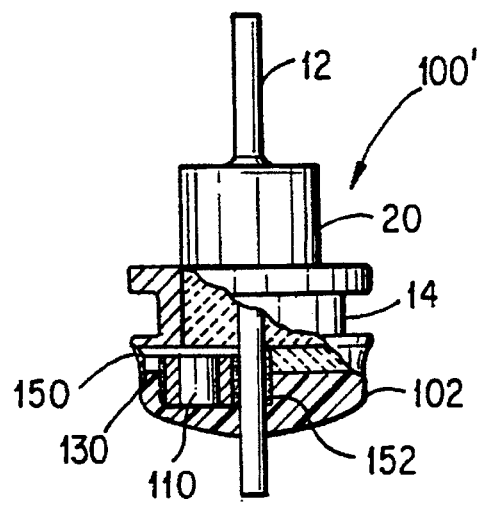
FIG. 11 is an elevation view, partially cut-away, of an alternate embodiment of a single lead version of the present invention employing the capacitor support assembly of FIG. 7.

Turning now to FIG. 11, there is shown, an alternate embodiment of the single lead filtered feedthrough device. The feedthrough 100' differs from the filtered feedthrough 100 in that the capacitor 110 is mounted to a substrate to form a capacitor support assembly 130 which may be tested prior to its mating with the conventional feedthrough. As shown in FIGS. 7 and 8, a substrate 132 is provided with an aperture 136 formed therethrough. When assembled to the feedthrough, the lead wire 12 will extend through the aperture 136 and be electrically connected to a metallized annular region 144 extending around the aperture 136. Substrate 132 has a surface 138 having a channel 134 defined thereon. Channel 134 provides a passage or guideway for locating placement of the chip capacitor 110. The channel 134 extends radially from the central aperture 136 to the perimeter edge of the substrate. Substrate 132 has a metallized edge surface 140 and a metallized region 142 disposed at the distal end of channel 134 electrically coupled to the metallized edge 140. By virtue of the metallization formed on substrate 132, the capacitor 110 may be joined thereto, by a process which is substantially identical to that described for the installation of the capacitor directly to the feedthrough device, with the exception of the additional steps required to mate the capacitor support assembly 132 to the feedthrough and the delay in applying the encapsulant until such mating has taken place.

Figure 9:
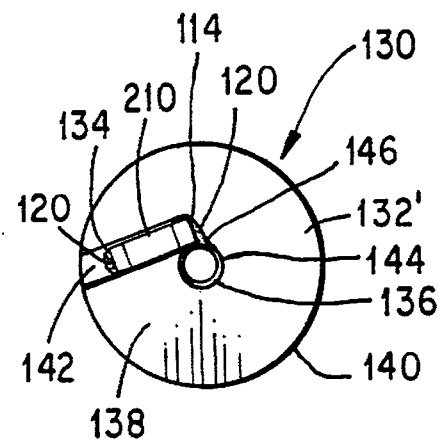
FIG. 9 is a bottom plan view of an alternate configuration of the capacitor support assembly of FIG. 7.

Thus, the capacitor 110 may have a non-conductive film applied to a side surface prior to its placement in the channel 134. Subsequent to such placement, the conductive metal 120 is applied to the opposing ends of capacitor 110 to electrically couple such to the respective metallization regions 142 and 144, by the methods previously described. Once the capacitor 110 has been installed on the substrate 132, the subassembly may be then subjected to testing, and if the electrical tests meet the appropriate specifications, then such may be assembled to the feedthrough device, such as the feedthrough 10, shown in FIG. 1. The capacitor support assembly 130 is disposed on the feedthrough with the lead 12 extending through the aperture 136, and the metallized edge 140 overlaying the end surface 18 of the ferrule 14. A non-conductive adhesive may be applied to the under surface of substrate 132 to affix the assembly 130 in position prior to the electrical connections being made, if desired. Electrically conductive material 150 is applied about the metallized perimeter 140 and a conductive material 152 is applied to the lead 12, adjacent the metallized annular region 144, to thereby electrically couple the capacitor 110 between the lead wire 12 and the ferrule 14. The electrically conductive material 150, 152 may be a material selected from the same group of materials which may be utilized to provide electrical coupling of the capacitor itself (material 120). Subsequent to installation of the capacitor support assembly 130, and any curing steps required for the conductive materials 150, 152, the device is then provided with encapsulant 102 to overlay the capacitor support assembly 130, including the capacitor itself, if the application requires such. As shown in FIG. 9, the capacitor support assembly 130 may have a substrate 132' which is configured to accommodate a larger chip capacitor 210. Substrate 132' is substantially identical to that of substrate 132, with the exception that the channel 134 is offset from the aperture 136 to permit the conductive side segment of the capacitor to be disposed adjacent aperture 136 to provide a completed filtered feedthrough having an arrangement like that described for the embodiment of FIG. 5. In this embodiment, the metallized region 144 includes an extension 146 which is disposed at the proximal end of the channel 134 to allow the capacitor to be electrically coupled to the metallized region 144 by application of the conductive material 120 to the metallized contact end surface 114. By this arrangement, the capacitor 210 may be pretested as part of the capacitor support assembly 130 prior to its being married to the feedthrough device.

In the embodiments of FIGS. 7, 8 and 9, the channel 134 is defined by a recess which is formed in the surface 138 of the substrate 132, 132'. Alternately, the channel 134 may be defined on the surface 138 in a region between a pair of ridges or raised portions 148. Like the recess, the raised portions 148 simply provide a locating guideway for placement of the chip capacitor. Such a guideway becomes particularly important when such a capacitor support assembly is utilized to form a multi-lead filtered feedthrough.

Figure 19:
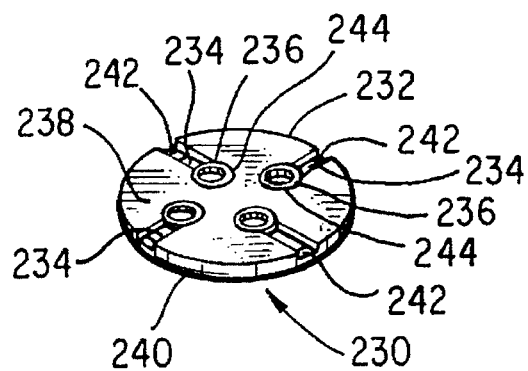
FIG. 19 is a perspective view of a multi-lead embodiment of the substrate shown in FIG. 8.
Figure 20:
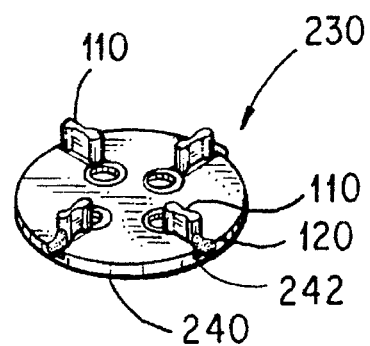
FIG. 20 is a perspective view of a multi-lead embodiment of a capacitor support assembly.
Figure 21:
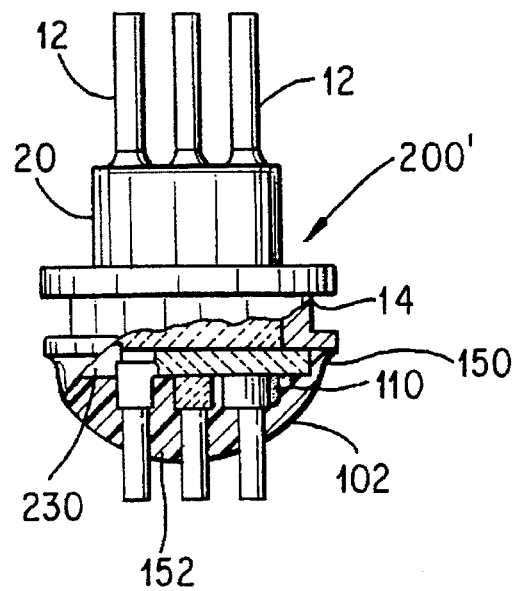
FIG. 21 is an elevation view, partially cut-away, of an alternate embodiment of the multi-lead version of the present invention employing the capacitor support assembly of FIG. 20.

Shown in FIG. 21, is multi-lead filtered feedthrough 200' which incorporates a capacitor support assembly 230, like that shown in FIG. 20. As in the single lead embodiment, capacitor support assembly 230 includes a substrate 232 having a surface 238 with a plurality of channels 234 formed thereon for positioning respective chip capacitors 110 (210). As shown in FIG. 19, substrate 232 is provided with a plurality of apertures 236, the number corresponding to the number of lead wires 12 of the particular feedthrough to which the assembly 230 is to be added. Substrate 232 includes a metallized perimeter edge 240 which is electrically coupled to metallization regions 242 disposed at the distal end of each channel 234. An annular metallized region 244 is disposed about each aperture 236 for coupling to a respective capacitor and lead wire.

Where multiple capacitors are being incorporated in a feedthrough device, it is particularly advantageous to have the ability to pretest a subassembly before final installation, so as not to have to scrap and thereby waste an entire device due to the failure of a single component. Therefore, after fixation of the capacitors 110 (210) to the substrate 232, or substantially simultaneous therewith, the conductive material 120 is applied to opposing ends of each capacitor, and the assembly heated to provide a partial cure of the conductive and non-conductive materials, as has been previously described. The capacitor support assembly 230 may then be electrically tested to insure that each capacitor is performing up to the required specifications. Subsequent to passing all testing, or after replacement of any defective capacitor, the assembly 230 may then be further exposed to a predetermined temperature to complete the curing process. Subsequently, the capacitor support assembly 230 is joined to the multi-lead feedthrough device, the substrate being juxtaposed over the end surfaces of the insulator and ferrule, secured thereto with a non-conductive adhesive and electrically coupled on the metallized perimeter edge 240 by conductive material 150, and the respective lead wires 12 by the conductive material 152. After appropriate curing, if necessary, an encapsulant 102 may be applied to overlay the assembly 230 and the capacitors carried thereby, followed by an appropriate curing operation.

Figure 23:
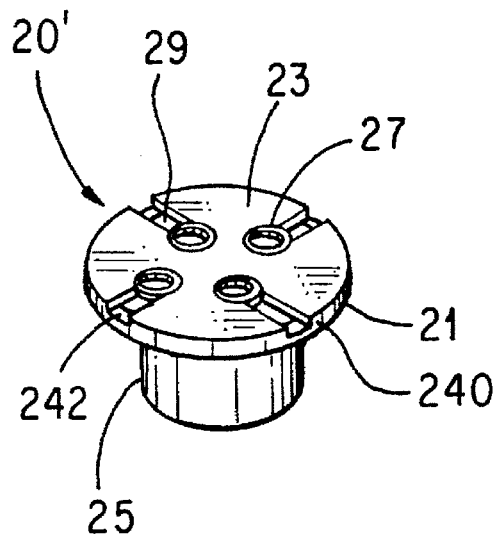
FIG. 23 is a perspective view of an alternate embodiment of a feedthrough insulator having an integral capacitor support.
Figure 24:
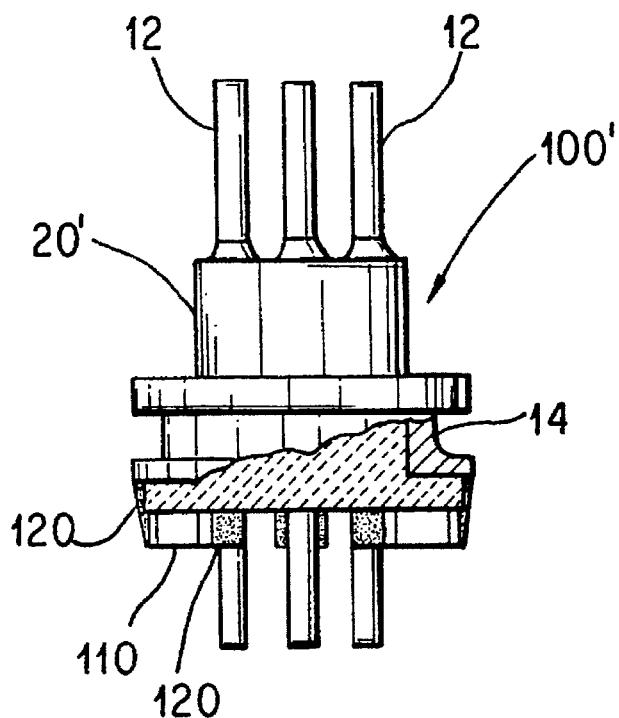
FIG. 24 is an elevation view, partially cut-away, of a multilead version of the present invention employing the insulator of FIG. 23.

The substrate of the capacitor support assembly may be formed integrally with the insulator of the feedthrough device, as shown in FIGS. 23 and 24. The feedthrough 100' is provided with an insulator 20', insulator 20' having a cylindrical body portion 25 which extends to a flanged portion 21. The end surface 23 of the flanged portion 21 defines the substrate portion onto which one or more chip capacitors 110, 210 are mounted. Thus, the insulator 20' is provided with one or more apertures 27, corresponding to the number of leads 12 of the feedthrough. As in the embodiments already described, an annular metallized region is formed about each aperture 27, and the perimeter edge of the flanged portion 21 also includes a metallized perimeter edge 240 having regions 242 which extend into a portion of each of the recesses 29. As shown in FIG. 24, the chip capacitors 110 are assembled to the feedthrough in the same manner as has already been described, with the capacitors being electrically coupled on opposing ends to the respective metallization portions formed on the insulator end surface 23 and/or the respective feedthrough lead 12 and the ferrule 14. Although a multilead structure is depicted, it should be understood that the insulator 20' may be provided with a single aperture for use with a single lead feedthrough device.

Figure 12:
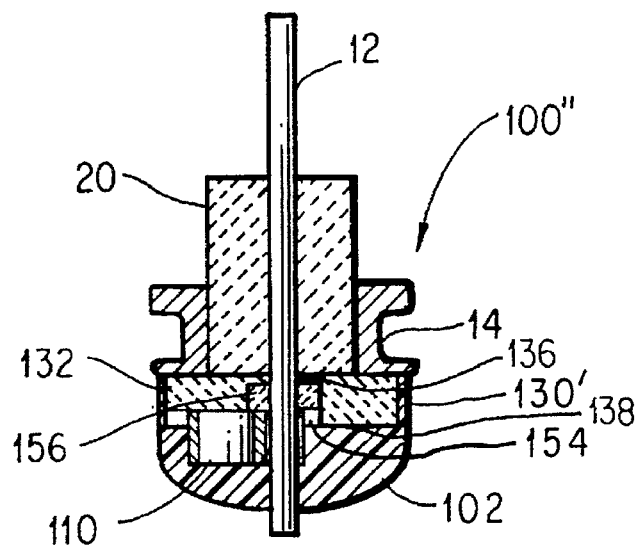
FIG. 12 is a cross-sectional elevation view of an alternate embodiment of the single lead version of the present invention showing an alternate embodiment of the capacitor support assembly of FIG. 7.
Figure 22:
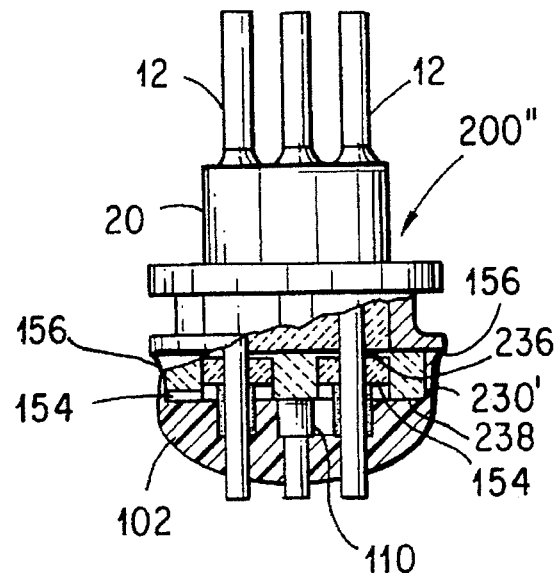
FIG. 22 is an elevation view, partially cut-away, of a multi-lead version of the present invention employing an alternate embodiment of the capacitor support assembly of FIG. 20.

The substrate 232, 20' may have one or more channels 234 configured like that provided on the substrate 132' or oriented to duplicate the capacitor orientation shown in FIGS. 16 and 18 in order to facilitate the utilization of chip capacitors of larger dimension. The substrates 132, 132', 232 may be formed of any insulating material capable of carrying metallization. However, due to the high reliability requirements for implantable medical devices, ceramic material compositions are preferred. Where a more complex filter circuit is desired, the substrate 132, 132', 232 may be formed of a ferrite material, or a ceramic/ferrite composition in order to add inductance to the filter circuit.

Where an inductive-capacitive filter circuit is desired, the capacitor support assembly may be modified to incorporate one or more ferrite beads 156, as shown in FIGS. 12 and 22. The capacitor support assemblies 130', 230' include recesses 154 disposed coaxially with respect to each aperture 136, 236, permitting the ferrite beads to be disposed below the surface 138, 238 of the respective substrate, so as not to interfere with the placement of the chip capacitors 110 thereon. Thus, the capacitor support assembly 130', 230' may carry a more complex filter and still be tested prior to its marriage with a respective conventional feedthrough device, and any defective component replaced. By this arrangement, many advantages are achieved over prior art devices.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A filtered feedthrough assembly for medical implantable devices, comprising:

a metallic ferrule having opposing first and second ends and a centrally disposed through opening extending between said first and second ends, said ferrule having a first flange formed on said first end for coupling to a medical implantable device and a second flange formed on said second end;

at least one elongate lead wire having a circular cross-sectional contour extending through said ferrule through opening;

means for forming a hermetic seal between said lead wire and said ferrule disposed within said ferrule through opening;

at least one chip capacitor having a parallelepiped contour extending from said lead wire to said second flange of said ferrule, said chip capacitor having a pair of metallized contacts formed on opposing end portions of said chip capacitor, each of said metallized contacts having conductive segments disposed on at least an end most portion of each side of said chip capacitor, said chip capacitor having one conductive segment of a respective endmost side portion disposed in contiguous relationship with said lead wire and one conductive segment on a lower side of said opposing end portion disposed contiguous said second flange of said ferrule; and, means for electrically coupling said metallized contacts to said lead wire and said second flange of said ferrule respectively.

2. The filtered feedthrough assembly as recited in claim 1 further comprising a non-conductive adhesive disposed on a bottom surface of said chip capacitor between said pair of metallized contacts.

3. A filtered feedthrough assembly for medical implantable devices, comprising:

a metallic ferrule having opposing first and second ends and a centrally disposed through opening extending between said first and second ends, said ferrule having a first flange formed on said first end for coupling to a medical implantable device and a second flange formed on said second end;

at least one elongate lead wire having a circular cross-sectional contour extending through said ferrule through opening;

means for forming a hermetic seal between said lead wire and said ferrule disposed within said ferrule through opening, said hermetic seal means having an end surface disposed in coplanar relationship with said second flange of said ferrule;

filter support means disposed at said end surface of said hermetic seal means, said filter support means including a insulative substrate having at least one aperture formed therein for passage of said lead wire therethrough;

at least one chip capacitor having a parallelepiped contour disposed on said filter support means extending from said lead wire to said second flange of said ferrule, said chip capacitor having a pair of metallized contacts formed on opposing end portions of said chip capacitor; and, means for electrically coupling said metallized contacts to said lead wire and said second flange of said ferrule respectively.

4. The filtered feedthrough assembly as recited in claim 3 where said hermetic seal means is formed of an insulative material composition.

5. The filtered feedthrough assembly as recited in claim 4 where said insulative material composition is a glass composition.

6. The filtered feedthrough assembly as recited in claim 4 where said insulative material composition is a ceramic material.

7. The filtered feedthrough assembly as recited in claim 3 where said filter support means includes a metallized annulus formed on said substrate surrounding said at least one aperture for electrical coupling with a first of said pair of metallized contacts and said at least one lead wire.

8. The filtered feedthrough assembly as recited in claim 7 where said filter support means includes a metallized region formed on said substrate adjacent a perimeter edge thereof for electrical coupling with a second of said pair of metallized contacts and said ferrule.

9. The filtered feedthrough assembly as recited in claim 3 where said insulative substrate and said hermetic seal means are integrally formed in one piece formation.

10. A multi-lead filtered feedthrough assembly for medical implantable devices, comprising:

a metallic ferrule having opposing first and second ends and a centrally disposed through opening extending between said first and second ends, said ferrule having a first flange formed on said first end for coupling to a medical implantable device and a second flange formed on said second end;

a plurality of elongate lead wires extending through said ferrule through opening, each of said plurality of lead wires having a circular cross-sectional contour;

means for forming a hermetic seal between said plurality of lead wires and said ferrule disposed within said ferrule through opening, said hermetic seal means having an end surface disposed in coplanar relationship with said second flange of said ferrule;

filter support means disposed at said end surface of said hermetic seal means, said filter support means including a insulative substrate having a plurality of apertures formed therein for respective passage of said plurality lead wires therethrough;

a plurality of chip capacitors, each of said plurality of chip capacitors being disposed on said filter support means and having a parallelepiped contour and extending from a respective one of said plurality of lead wires to said second flange of said ferrule, each of said chip capacitors having a pair of metallized contacts formed on opposing end portions of said chip capacitor; and, means for electrically coupling said metallized contacts of each of said chip capacitors respectively to a respective one of said lead wires and said ferrule.

11. The filtered feedthrough assembly as recited in claim 10 where said insulative substrate and said hermetic seal means are integrally formed in one piece formation.

12. The multi-lead filtered feedthrough assembly as recited in claim 10 further comprising a plurality of bands of a nonconductive material disposed on an end surface of said hermetic seal means, each of said plurality of bands of nonconductive material being disposed adjacent one side of a respective one of said plurality of chip capacitors.

13. The multi-lead filtered feedthrough assembly as recited in claim 12 where each of said plurality of bands of nonconductive material is formed by a polyimide composition.

14. The multi-lead filtered feedthrough assembly as recited in claim 12 where each of said plurality of bands of nonconductive material is formed by an epoxy composition.

15. The multi-lead filtered feedthrough assembly as recited in claim 10 where said extension of each of said chip capacitors forms an angle $\theta$ with respect to a respective radial line extending from a central axis of said ferrule through a respective lead wire, said angle $\theta$ being within a range $0°<\theta<90°$.

16. The filtered feedthrough assembly as recited in claim 10 where said filter support means includes a plurality of metallized annuluses respectively formed on said substrate surrounding said plurality of apertures, each of said metallized annuluses providing electrical coupling with a first of said pair of metallized contacts of a respective one of said plurality of chip capacitors and a respective one of said plurality of lead wires.

17. The filtered feedthrough assembly as recited in claim 16 where said filter support means includes a metallized region formed on said substrate adjacent a perimeter edge thereof for electrical coupling with a second of said pair of metallized contacts of each of said plurality of chip capacitors and said ferrule.

18. A multi-lead filtered feedthrough assembly for medical implantable devices, comprising:

a longitudinally extended metallic ferrule having opposing first and second ends and a centrally disposed through opening extending between said first and second ends, said ferrule having a flange formed on said first end for coupling to a medical implantable device;

a plurality of elongate lead wires extending through said ferrule through opening in radially spaced relationship with respect to a longitudinal axis of said ferrule, each of said plurality of lead wires having a circular cross-sectional contour;

means for forming a hermetic seal between said plurality of lead wires and said ferrule disposed within said ferrule through opening, said hermetic seal means having an end surface disposed in coplanar relationship with said second end of said ferrule;

a plurality of chip capacitors disposed on said end surface of said hermetic seal means, each of said plurality of chip capacitors having a parallelepiped contour and extending from a respective one of said plurality of lead wires to said ferrule, said extension of each of said chip capacitors forming an angle $\theta$ with respect to a respective radial line extending from said longitudinal axis of said ferrule through a respective lead wire, said angle $\theta$ being within a range $0°<\theta<90°$, each of said chip capacitors having a pair of metallized contacts formed on opposing end portions of said chip capacitor; and means for electrically coupling said metallized contacts of each of said chip capacitors respectively to a respective one of said lead wires and said ferrule.

19. The multi-lead filtered feedthrough assembly as recited in claim 18 further comprising a plurality of bands of a nonconductive material disposed on said end surface of said hermetic seal means, each of said plurality of bands of nonconductive material being disposed adjacent one side of a respective one of said plurality of chip capacitors.

20. The multi-lead filtered feedthrough assembly as recited in claim 19 where each of said plurality of bands of nonconductive material is formed by an epoxy composition.

21. The multi-lead filtered feedthrough assembly as recited in claim 19 where each of said plurality of bands of nonconductive material is formed by a polyimide composition.

22. The multi-lead filtered feedthrough assembly as recited in claim 18 where each of said metallized contacts have conductive segments disposed on at least an end most portion of each side of said chip capacitor, each of said chip capacitors having one endmost side portion disposed in contiguous relationship with a respective one of said plurality of lead wires.

23. A method of adding chip capacitor filters to a feedthrough assembly for use in medical implantable devices, comprising the steps of:
   a. providing an insulative substrate, said substrate having at least one aperture and at least one channel extending from said aperture to a perimeter edge thereof;
   b. providing at least one parallelepiped shaped chip capacitor, said chip capacitors having a pair of metallized contacts formed on opposing end portions of said chip capacitor;
   c. installing said chip capacitor on said insulative substrate in said channel;
   d. providing a feedthrough assembly having a ferrule, at least one lead wire extending through an opening formed in said ferrule, and means for hermetically sealing said lead wire and said ferrule, said hermetic sealing means having an end surface disposed in coplanar relationship with an end of said ferrule;
   e. positioning said substrate on said end surface of said hermetic sealing means with said lead wire passing through said aperture; and,
   f. electrically coupling said pair of metallized contacts respectively to said lead wire and said ferrule.

24. The method as recited in claim 23 where said step of installing said chip capacitor is followed by the step of electrically testing said chip capacitor.

25. A method of adding chip capacitor filters to a multi-lead feedthrough assembly for use in medical implantable devices, comprising the steps of:
   a. providing a feedthrough assembly having a ferrule, a plurality of lead wires extending through an opening formed in said ferrule, and means for hermetically sealing said plurality of lead wires and said ferrule;
   b. providing a plurality of parallelepiped shaped chip capacitors, each of said chip capacitors having a pair of metallized contacts formed on opposing end portions of said chip capacitor, each of said pair of metallized contacts having conductive segments disposed on at least an end most portion of each side of said chip capacitor;
   c. installing each of said plurality of chip capacitors between a respective lead wire and an end surface of a flange of said ferrule, said step of installing each chip capacitor includes applying a nonconductive film to a bottom surface of a respective chip capacitor, positioning a respective chip capacitor to extend between a respective one of said lead wires and said ferrule, applying an electrically conductive material to bridge between a first of said pair of metallized contacts and said respective lead wire, applying an electrically conductive material to bridge between a second of said pair of metallized contacts and said ferrule, and heating said feedthrough with said positioned chip capacitors at a first predetermined temperature to at least partially cure said nonconductive film;
   d. electrically testing said installation of each of said chip capacitors; and,
   e. heating said feedthrough with said positioned chip capacitors at a second predetermined temperature, said second predetermined temperature being higher than said first predetermined temperature.

26. The method as recited in claim 25 where the step of applying an electrically conductive material includes the step of applying an electrically conductive adhesive.

27. A method of adding chip capacitor filters to a multi-lead feedthrough assembly for use in medical implantable devices, comprising the steps of:
   a. providing a feedthrough assembly having a ferrule, a plurality of lead wires extending through an opening formed in said ferrule, and means for hermetically sealing said plurality of lead wires and said ferrule;
   b. providing a plurality of parallelepiped shaped chip capacitors, each of said chip capacitors having a pair of metallized contacts formed on opposing end portions of said chip capacitor, each of said pair of metallized contacts having conductive segments disposed on at least an end most portion of each side of said chip capacitor; and,
   c. installing each of said plurality of chip capacitors between a respective lead wire and an end surface of a flange of said ferrule, said step of installing each chip capacitor includes placing one of said side conductive segments of said first metallized contact of each chip capacitor contiguous a respective lead wire and placing one conductive segment of a lower side of said opposing end portion contiguous said end surface of said flange of said ferrule.

28. A method of adding chip capacitor filters to a multi-lead feedthrough assembly for use in medical implantable devices, comprising the steps of:
   a. providing a feedthrough assembly having a ferrule, a plurality of lead wires extending through an opening formed in said ferrule, and means for hermetically sealing said plurality of lead wires and said ferrule;
   b. providing a plurality of parallelepiped shaped chip capacitors, each of said chip capacitors having a pair of metallized contacts formed on opposing end portions of said chip capacitor, each of said pair of metallized contacts having conductive segments disposed on at least an end most portion of each side of said chip capacitor; and,
   c. installing each of said plurality of chip capacitors between a respective lead wire and an end surface of a flange of said ferrule, said step of installing each chip capacitor includes extending each chip capacitor from a respective lead wire to said ferrule to form an angle $\theta$ with respect to a respective radial line extending from a central axis of said ferrule through said lead wire, said angle $\theta$ being within a range $0° < \theta < 90°$.

29. The method as recited in claim 28 where the step of installing each chip capacitor is preceded by the step of applying a plurality of bands of an insulating material to said end surface of said hermetic sealing means.

30. The method as recited in claim 29 where the step of applying a plurality of bands of an insulating material is followed by the step of heating said feedthrough to cure said insulating material.

31. A filtered feedthrough assembly for medical implantable devices, comprising:
   a metallic ferrule having opposing first and second ends and a centrally disposed through opening extending between said first and second ends, said ferrule having a first flange formed on said first end for coupling to a medical implantable device and a second flange formed on said second end;

at least one elongate lead wire having a circular cross-sectional contour extending through said ferrule through opening;

means for forming a hermetic seal between said lead wire and said ferrule disposed within said ferrule through opening, said hermetic seal means having an end surface disposed in coplanar relationship with said second flange of said ferrule;

filter support means disposed at said end surface of said hermetic seal means, said filter support means including a insulative substrate having at least one aperture formed therein for passage of said lead wire therethrough, said substrate having at least one channel formed thereon extending from said aperture to a perimeter edge thereof;

at least one chip capacitor having a parallelepiped contour disposed in said channel and extending from said lead wire to said ferrule, said chip capacitor having a pair of metallized contacts formed on opposing end portions of said chip capacitor; and, means for electrically coupling said metallized contacts to said lead wire and said second flange of said ferrule respectively.

32. The filtered feedthrough assembly as recited in claim 31 where said filter support means includes a metallized annulus formed on said substrate surrounding said aperture for electrical coupling with a first of said pair of metallized contacts and said lead wire.

33. The filtered feedthrough assembly as recited in claim 32 where said filter support means includes a metallized region formed on said substrate adjacent said perimeter edge thereof for electrical coupling with a second of said pair of metallized contacts and said ferrule.

34. The filtered feedthrough assembly as recited in claim 31 where said substrate is formed of a ferrite material.

35. The filtered feedthrough assembly as recited in claim 31 where said substrate is formed of a ceramic material.

36. The filtered feedthrough assembly as recited in claim 35 where said substrate has a recess surrounding said aperture.

37. The filtered feedthrough assembly as recited in claim 36 where said filter support means further includes a ferrite bead disposed in said recess and surrounding said lead wire.

38. The filtered feedthrough assembly as recited in claim 31 further comprising a plurality of lead wires and a plurality of chip capacitors respectively coupled thereto, each of said plurality of chip capacitors being disposed in a respective channel formed on said substrate.

39. The filtered feedthrough assembly as recited in claim 31 where said insulative substrate and said hermetic seal means are integrally formed in one piece formation.

40. A multi-lead filtered feedthrough assembly for medical implantable devices, comprising:

a metallic ferrule having opposing first and second ends and a centrally disposed through opening extending between said first and second ends, said ferrule having a first flange formed on said first end for coupling to a medical implantable device and a second flange formed on said second end;

a plurality of elongate lead wires extending through said ferrule through opening, each of said plurality of lead wires having a circular cross-sectional contour;

means for forming a hermetic seal between said plurality of lead wires and said ferrule disposed within said ferrule through opening;

a plurality of chip capacitors, each of said plurality of chip capacitors having a parallelepiped contour and extending from a respective one of said plurality of lead wires to said second flange of said ferrule, each of said chip capacitors having a pair of metallized contacts formed on opposing end portions of said chip capacitor, each of said metallized contacts having conductive segments disposed on at least an end most portion of each side of said chip capacitor, each of said chip capacitors having one conductive segment of a respective endmost side portion disposed in contiguous relationship with a respective one of said plurality of lead wires and one conductive segment on a lower side of said opposing end portion disposed contiguous said second flange of said ferrule; and, means for electrically coupling said metallized contacts of each of said chip capacitors respectively to a respective one of said lead wires and said ferrule.

* * * * *